United States Patent
Young et al.

(10) Patent No.: US 9,212,059 B2
(45) Date of Patent: Dec. 15, 2015

(54) METHOD AND APPARATUS FOR IMPROVING THE EFFICIENCY OF AN SMR PROCESS FOR PRODUCING SYNGAS WHILE REDUCING THE $CO_2$ IN A GASEOUS STREAM

(71) Applicant: Gyco, Inc., Cedar Rapids, IA (US)

(72) Inventors: Gary C. Young, Cedar Rapids, IA (US); Eric S. Wagner, La Canada, CA (US); John C. Wooley, Austin, TX (US)

(73) Assignee: Gyco, Inc., Cedar Rapids, IA (US)

( * ) Notice: Subject to any disclaimer, the term of this patent is extended or adjusted under 35 U.S.C. 154(b) by 0 days.

(21) Appl. No.: 14/224,842

(22) Filed: Mar. 25, 2014

(65) Prior Publication Data

US 2014/0288196 A1  Sep. 25, 2014

Related U.S. Application Data

(63) Continuation-in-part of application No. 13/963,857, filed on Aug. 9, 2013, now Pat. No. 8,916,617, which is a continuation of application No. 13/085,175, filed on Apr. 12, 2011, now Pat. No. 8,507,567, which is a (Continued)

(51) Int. Cl.
*C01B 3/48* (2006.01)
*C07C 29/151* (2006.01)
(Continued)

(52) U.S. Cl.
CPC ... *C01B 3/48* (2013.01); *C01B 3/34* (2013.01); *C01B 2203/00* (2013.01);
(Continued)

(58) Field of Classification Search
CPC ............ C01B 2203/00; C01B 2203/02; C01B 2203/0205; C01B 2203/0211; C01B 2203/0222; C01B 2203/06; C01B 2203/061; C01B 2203/062; C01B 3/02; C01B 3/32; C01B 3/323; C01B 2203/0216; C01B 2203/0233

See application file for complete search history.

(56) References Cited

U.S. PATENT DOCUMENTS 4,166,786 A  9/1979  Duraiswamy et al.
4,752,623 A  6/1988  Stevens et al.

(Continued)

FOREIGN PATENT DOCUMENTS

WO  9711904  4/1997
WO  2005001977 A1  1/2005
WO  2007022639 A1  3/2007

OTHER PUBLICATIONS

Jing, Q.S., et al., EEffective reforming of methane with CO2 and O2 to low H2/CO ratio syngas over Ni/MfO—SiO using fluidized bed reactor, 2004, Energy Conversation & Management, 45, pp. 3127-3137.*

(Continued)

*Primary Examiner* — Yate K Cutliff
(74) *Attorney, Agent, or Firm* — Slater & Matsil, L.L.P.

(57) ABSTRACT

A system and method for increasing the production of Syngas from an SMR (Steam Methane Reforming) processing plant by providing $CO_2$ as an additional feedstock, such as from an exhaust stream of a Corn-to-Ethanol plant, or from a power plant or industrial plant, like a cement plant. The $CO_2$ steam and methane are introduced into the SMR reactor heated to about 870° C. and at about one atmosphere such that a reaction takes place that produces Syngas comprising CO, Hydrogen ($H_2$) and carbon dioxide ($CO_2$). The Syngas is then cleaned and provided to a Fischer-Tropsch synthesis reactor or other Bio-catalytic synthesis reactor to produce Ethanol or other high value liquid fuel.

18 Claims, 2 Drawing Sheets

Related U.S. Application Data continuation of application No. 12/271,227, filed on Nov. 14, 2008, now Pat. No. 7,932,298, which is a continuation-in-part of application No. 11/956,107, filed on Dec. 13, 2007, now Pat. No. 7,923,476.

(51) Int. Cl.
   *C12P 7/06* (2006.01)
   *C01B 3/34* (2006.01)

(52) U.S. Cl.
   CPC ............... *C01B 2203/0205* (2013.01); *C01B 2203/0216* (2013.01); *C01B 2203/0222* (2013.01); *C01B 2203/0283* (2013.01); *C01B 2203/049* (2013.01); *C01B 2203/0415* (2013.01); *C01B 2203/0465* (2013.01); *C01B 2203/0485* (2013.01); *C01B 2203/06* (2013.01); *C01B 2203/061* (2013.01); *C01B 2203/062* (2013.01); *C01B 2203/84* (2013.01); *C01B 2203/86* (2013.01); *C07C 29/1518* (2013.01); *C12P 7/06* (2013.01); *Y02E 50/17* (2013.01)

(56) References Cited

U.S. PATENT DOCUMENTS

| | | | |
|---|---|---|---|
| 4,888,130 A * | 12/1989 | Banquy | 252/373 |
| 5,496,859 A * | 3/1996 | Fong et al. | 518/703 |
| 5,937,652 A | 8/1999 | Abdelmalek | |
| 6,328,945 B1 * | 12/2001 | Hufton et al. | 423/418.2 |
| 6,527,980 B1 * | 3/2003 | Roden et al. | 252/373 |
| 2002/0155061 A1 * | 10/2002 | Prasad et al. | 423/652 |
| 2004/0018144 A1 | 1/2004 | Briscoe | |
| 2006/0143980 A1 | 7/2006 | Rapier et al. | |
| 2006/0191201 A1 * | 8/2006 | Berggren et al. | 48/197 R |
| 2007/0004809 A1 * | 1/2007 | Lattner et al. | 518/700 |
| 2007/0099038 A1 | 5/2007 | Galloway | |
| 2007/0137107 A1 | 6/2007 | Barnicki | |
| 2007/0254969 A1 | 11/2007 | Olah et al. | |
| 2008/0169449 A1 | 7/2008 | Mundschau | |
| 2008/0307703 A1 | 12/2008 | Dietenberger et al. | |
| 2009/0156695 A1 | 6/2009 | Young | |
| 2009/0170968 A1 | 7/2009 | Nahas et al. | |
| 2009/0221720 A1 | 9/2009 | Belt et al. | |
| 2009/0221721 A1 | 9/2009 | Norbeck et al. | |
| 2010/0137459 A1 | 6/2010 | Stites et al. | |
| 2010/0200810 A1 | 8/2010 | Schmidt et al. | |
| 2011/0067306 A1 | 3/2011 | Balmas et al. | |
| 2011/0186783 A1 | 8/2011 | Young | |

OTHER PUBLICATIONS

Rahimpour, M.R., et al., Synthesis gas production in a novel hydrogen and oxygen perm-selective memtranes tri-reformer for methanol production, 2012, Journal of Natural Gas Science and Engineering, vol. 9, pp. 149-159.*

Bengelsdorf, F., et al., Bacterial synthesis gas fermentation, 2013, Environmental Technology, 34:13-14, pp. 1639-1651.*

Spath, P., et al., Products from syngas-methanol, 2008, Sungrant Bioweb, 10 pages.*

Choudhary, V.R., et al., "Simultaneous steam and CO2 reforming of methane to syngas over NiO/MgO/SA-5205 in present and absence of oxygen," Applied Catalysis A: General 168, 1998, pp. 33-46.

ConocoPhillips Technology Solutions, Mar. 2004, 15 pgs.

Higman, C., et al., "Gasification: The Thermodynamics of Gasification," Second edition, 2008, Elsevier Publishing, 5 pages.

Holt, N , "Gasification Process Selection- Trade-Offs and Ironies." Presented at the Gasification Technologies Conference 2004, Oct. 3-6, 2004, pp. 1-10, JW Marriott Hotel, Washington, DC.

International Search Report and Written Opinion received in Patent Cooperation Treaty Application No. PCT/US2012/37775, Applicant: Gyco, Inc., mailing date: Aug. 9, 2012, 9 pages.

Jing, Q.S., et al., Effective reforming of methane with C02 and 02 to low H2/CO ratio syngas over Ni/MfO—SiO using fluidized bed reactor, 2004, Energy Conversation & Management, 45, pp. 3127-3137.

L.-Q., E., "Plasma Processing of Municipal Solid Waste," Brazilian Journal of Physics, vol. 34, No. 4B, Dec. 2004, pp. 1587-1593.

Lemonidou, A.A., et al., "Carbon dioxide reforming of methane over 5 wt.% Ni/CaO—Al2O3 catalyst," Applied Catalysis A: General 228, 2002, pp. 227-235.

Rahimpour, M.R., et al., Synthesis gas production in a novel hydrogen and oxygen perm-selective membranes tri-reformer for methanol production, 2012, Journal of Natural Gas Science and Engineering, vol. 9, pp. 149-159.

Roine, A., et al., "HSC Chemistry ® v.5.0," Chemical Reaction and Equilibrium Software with Extensive Thermochemical Database Product Instruction Manual, Jun. 28, 2002, Chapters 11, 13 and 14, 44 pages, Outokumpu Research Oy.

Rosenberg, W.G., et al., "Financing IGCC—3 Party Covenant," BSCIA Working Paper Jan. 2004, Energy Technology Innovation Project, Belfer Center for Science and International Affairs, Feb. 2004, 143 pgs, John F. Kennedy School of Government, Harvard University, Cambridge, MA.

Stiegel, G.J., "Gasification—Versatile Solutions: Gasification Technologies Overview," NASEO 2006 Annual Meeting, Seattle, Washington, Sep. 10-13, 2006, 35 pages, National Energy Technology Laboratory.

"Technology Evaluation and Economic Analysis of Waste Tire Pyrolysis, Gasification and Liquefaction," Integrated Waste Management Board, Contractor•s Report, Mar. 2006, University of California Riverside, 103 pages.

URS Corporation, "Summary Report: Evaluation of Alternative Solid Waste Processing Technologies," Prepared for City of Los Angeles, Department of Public Works Bureau of Sanitation, Sep. 2005, 40 pages, Los Angeles, CA.

Van Bibber, L., et al., "Baseline Technical and Economic Assessment of a Commercial Scale Fischer-Tropsch Liquids Facility," DOE/NETL-2007/1260, Final Report, Apr. 9, 2007, 79 pgs.

Young, G., "From Waste Solids to Fuel," Pollution Engineering Magazine, Feb. 2008, 4 pages.

Young, G.C., "How Trash Can Power Ethanol Plants," Public Utilities Fortnightly, Feb. 2007, pp. 72-74, 76.

Young, G.C., "Zapping MSW with Plasma Arc: An economical evaluation of a new technology for municipal solid waste treatment facilities," Pollution Engineering, Nov. 2006, pp. 26-29.

* cited by examiner

METHOD AND APPARATUS FOR IMPROVING THE EFFICIENCY OF AN SMR PROCESS FOR PRODUCING SYNGAS WHILE REDUCING THE $CO_2$ IN A GASEOUS STREAM

This application is a continuation-in-part of patent application Ser. No. 13/963,857 filed Aug. 9, 2013 which is a continuation of patent application Ser. No. 13/085,175 filed Apr. 12, 2011 and issued as U.S. Pat. No. 8,507,567, which is a continuation of patent application Ser. No. 12/271,227 filed Nov. 14, 2008, issued as U.S. Pat. No. 7,932,298, which is a continuation-in-part of patent application Ser. No. 11/956,107, filed Dec. 13, 2007 and issued as U.S. Pat. No. 7,923,476, which applications are hereby incorporated herein by reference.

TECHNICAL FIELD

The present invention relates generally to GTL (Gas To Liquid) feedstock preparation and more specifically to improving the efficiency of the SMR (Steam Methane Reforming) process while at the same time reducing the presence of carbon dioxide ($CO_2$). In a specific embodiment, the carbon dioxide such as from a biomass fermenter (such as an Ethanol fermenter) or a gaseous exhaust stream from power plants and other types of industrial plants is reduced while increasing the efficiency of the SMR (Steam Methane Reforming) process for forming a Syngas ($CO+H_2$). The syngas, in turn, can be used in the production of liquid fuels, such as for examples only, Ethanol, Diesel, Methanol, Butanol, Jet Fuel, Gasoline and other.

BACKGROUND

Concern about global warming eventually leads to discussions about the need to reduce the amount of carbon dioxide that pours into the earth's atmosphere on a daily basis from power plants and other industrial factories. At the same time, concerns about dwindling supplies of fossil fuels have encouraged the development of liquid fuels such as Ethanol as future replacement fossil fuels. The cost of preparation of feedstock, such as syngas generation is typically the most expensive part of GTF (Gas to Liquid) methods of producing a liquid fuel such as Ethanol. In the SMR process this cost typically represents about 50% of the total CAPEX (Capital Expense). Further the present SMR process is not particularly efficient and, unfortunately, results in as much or more carbon dioxide being introduced into the atmosphere as does burning fossil fuels.

The SMR process is a mature "catalytic" process that operates at about 870 degrees C. (1,600 degrees F.) and at pressures of between about 35 psig and 550 psig. As will be appreciated by those skilled in the art, the SMR process has been optimized for productivity and efficiency over many years of industrial applications. However, the process is limited to the use of gaseous and/or liquid feed-stocks only, and primarily operates on Methane gas as a Carbonaceous feedstock to produce Syngas (CO and $H_2$). An F-T [Fischer-Tropsch] converter) is typically used with the SMR process to convert the resulting Syngas to Ethanol. Some existing SMR plants feedback the exhaust or tail gas from the F-T converter to the SMR reaction chamber to control, balance or selectively adjust the ratio of the $H_2$ and CO in the resulting Syngas. Adjusting or balancing the $H_2/CO$ ratio of the Syngas is often desired or necessary because the Syngas leaving the SMR reactor typically contains an excess of $H_2$ for efficient conversion by the F-T reactor. However, until this invention a separate stream of $CO_2$ has never been used as an additional feed-stock.

The SMR reaction is:

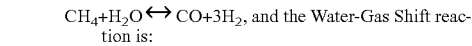
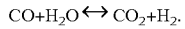

$$CO+H_2O \leftrightarrow CO_2+H_2.$$

Therefore, a method for more efficiently producing a Syngas, (easily convertible to Ethanol and other liquid fuels) by the SMR process while at the same time removing $CO_2$ from gaseous streams exhausted by industrial plants would offer many advantages in cost, as well as, an overall reduction in the carbon dioxide dumped into the atmosphere.

SUMMARY OF THE INVENTION

The present invention discloses methods and apparatus for reducing the carbon dioxide that is often present in an industrial gaseous streams exhausted or emitted from a biomass fermenter and other various power plants and types of industrial plants, such as (for example only) a cement plant. For example, the typical gaseous exhaust stream of about 400,000 lbs/hr total from an industrial cement plant will contain about 30%-40% (about 160,000 lbs/hr) of carbon dioxide ($CO_2$). However, instead of being exhausted to the atmosphere, according to this invention, the gaseous stream from a biomass fermenter, or any other source of $CO_2$ is provided to the reaction chamber of an SMR processing plant where at least a portion is converted to Syngas and thereby significantly increases the efficiency of an SMR (Steam Methane Reforming) plant. In addition to the normal chemical reactions that take place in a standard SMR process (i.e. $CH_4+H_2O \leftrightarrow CO+3H_2$ and $CO+H_2O \leftrightarrow CO_2+H_2$), the CO2 added as a feed-stock results in another reaction ($CO_2+H_2 \leftrightarrow CO+H_2O$) taking place in the chamber such that the $CO_2$ from the gaseous stream is also converted to CO in the Syngas. The Syngas can then be used as a feedstock for the production of Ethanol.

For example, a bio-catalytic process, or a catalytic process such as a Fischer-Tropsch process could be used to produce the Ethanol.

Simply put, this inventive process reduces the carbon dioxide in the atmosphere and increases the formation of Syngas in an SMR plant by introducing $CO_2$ into the SMR reaction chamber as an original feedstock along with the normal SMR feeds of methane, steam and oxygen.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

The making and using of the various embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Figure 1:
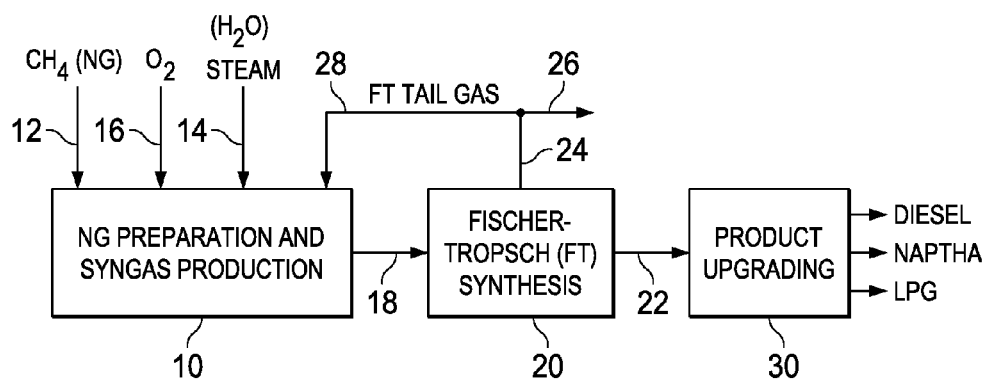
FIG. 1 is a simplified block diagram illustrating the standard SMR process.

Referring now to FIG. 1 there is shown a simplified block diagram of a standard well known SMR processing plant that includes the reaction chamber 10 that receives its carbonaceous input from a methane source at input 12. The reaction chamber 10 further receives steam ($H_2O$) at input 14 and oxygen $O_2$ (if necessary) at input 16. As is well known in the art, SMR plants produce syngas primarily comprised of carbon monoxide (CO), hydrogen ($H_2$) and Carbon Dioxide ($CO_2$) at output 18. The syngas output is then typically provided to a Fischer-Tropsch reactor 20 to produce Ethanol at output 22. In addition, the Fischer-Tropsch process may produce a tail gas, indicated at 24, that contains $CO_2$ along with CO, $H_2$ and $CH_4$. This tail gas may be used as a purge gas, burned as a heat source, vented to the atmosphere or collected and sequestered or otherwise disposed of as indicated at 26. Alternately, about one third of the tail gas may be recycled back to the SMR reactor as shown at 28.

In some existing SMR plants about one third of the exhaust or tail gas 24 from the F-T converter is provided to the SMR reaction chamber 10 to control, balance or selectively adjust the ratio of the $H_2$ and CO in the resulting Syngas. Adjusting or balancing the $H_2$/CO ratio of the Syngas is often desired or necessary because the Syngas leaving the SMR reactor typically contains an excess of $H_2$ that prevents the most efficient conversion by the F-T reactor which prefers a higher level of CO.

The Ethanol from the F-T reactor, or Methanol, may then be provided to a product upgrading step as shown at block 30 to convert the Ethanol or Methanol to other liquid products such as LPG, Diesel, Naptha, etc.

Figure 2:
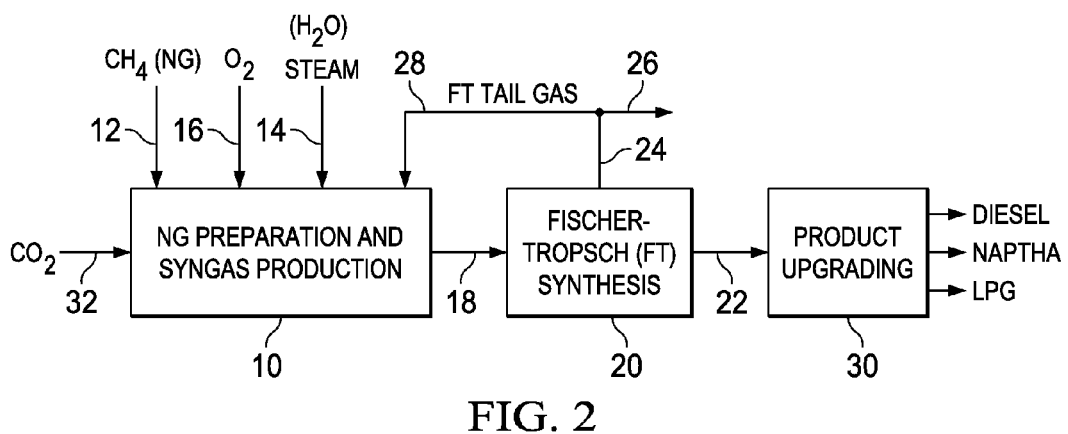
FIG. 2 is the same simplified block diagram of an SMR process as FIG. 1 except that it includes the addition of $CO_2$ as a reactant introduced into the SMR chamber to increase the efficiency of the process while consuming $CO_2$.

As shown in FIG. 2, and according to the present invention, there is illustrated a simplified block diagram of the same SMR plant discussed with respect to FIG. 1, except that it further incorporates the improvement of the present invention such that CO is formed by both the feed-stock of $CO_2$ combining with methane and the normal SMR reaction of Steam and Methane. The improved SMR processing operates at between about 700 degrees centigrade and 1,000 degrees centigrade, and between about 35 psig and 450 psig.

The process of this invention increases the $H_2$/CO ratio and consequently the amount of Ethanol production, while consuming and removing $CO_2$ from the atmosphere. More specifically, as shown, the addition of a $CO_2$ stream to the SMR chamber 10 at input 32 may be from biomass reactor or other industrial plant or source, such as for example only, a cement plant. That is, instead of being exhausted to the atmosphere, sequestered or otherwise disposed of, according to this invention, the gaseous $CO_2$ stream 32 is provided to the reaction chamber 10 of an SMR processing plant. In addition to the normal reactions of a standard SMR process (i.e. $CH_4 + H_2O \leftrightarrow CO + 3H_2$ and $CO + H_2O \leftrightarrow CO_2 + H_2$), the $CO_2$ added as a feed-stock results in another, reaction ($CO_2 + H_2 \leftrightarrow CO + H_2O$) taking place in the chamber such that the $CO_2$ from the gaseous stream is also converted to Syngas (CO+$H_2$). That is, the carbon (C) provided by the methane ($CH_4$) source 12 combines with one of the oxygen (O) atoms of the carbon dioxide ($CO_2$) molecules to form two molecules of carbon monoxide (2 CO) which, of course also reduces the amount of carbon dioxide ($CO_2$) in the reaction chamber. In the case of methane, in addition to the normal carbon monoxide, more hydrogen is produced (i.e. $3H_2$). It will also be appreciated that it is not likely that all of the added or reformed carbon dioxide ($CO_2$) will be converted to 2CO (i.e. carbon monoxide). However, the steam ($H_2O$) may also react with some of the carbon monoxide (CO) to reform some carbon dioxide ($CO_2$) and some hydrogen ($H_2$). Consequently, the reaction chamber discharges Syngas as indicated on line 18 comprised of carbon monoxide (CO), hydrogen ($H_2$) and a reduced amount of carbon dioxide ($CO_2$) to a reactor 20, such as a Fischer-Tropsch reactor.

Thus, it is seen that at this stage of the process the carbon dioxide ($CO_2$) has been reduced and the carbon monoxide (CO) in the Syngas increased. This provides a significant economic advantage, since as has been discussed; some biocatalytic processes are more effective using Syngas with a higher percentage of carbon monoxide (CO) as feed stock.

Figure 3:
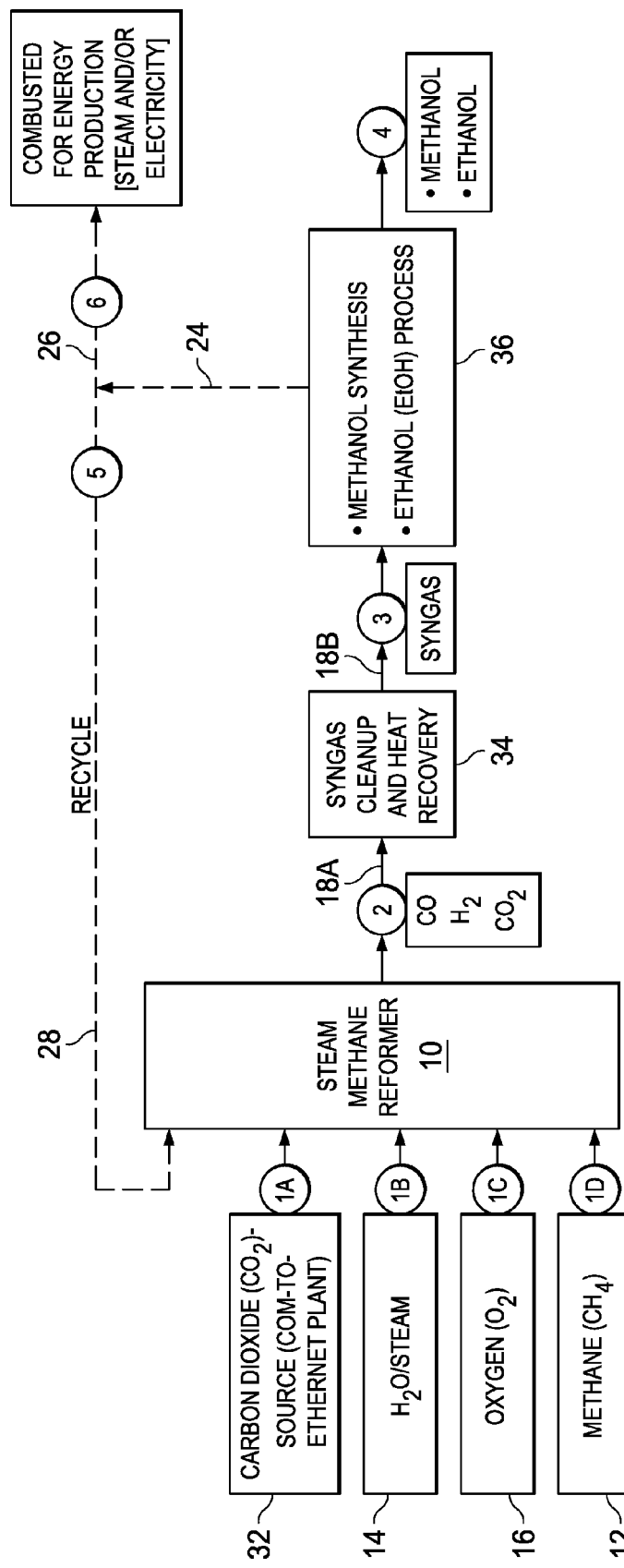
FIG. 3 is a more detailed illustration of the process of FIG. 2 for the production of Ethanol.

Referring now to FIG. 3, there is shown a more detailed version of the process of FIG. 2. Components, processes and conduits that are the same as in FIG. 2 are identified by the same reference numbers. As shown, the Syngas from the SMR reactor 10 is provided by line 18A to a Syngas Cleanup and Heat Recovery process 34 and then provided on Line 18B to a Methanol Synthesis or Ethanol Process, such as a Fischer-Tropsch synthesis reactor shown as block 36. As known by those skilled in the art, the Fischer-Tropsch reactor may be used to convert the Syngas to Ethanol 56. Alternately, a biochemical reactor could be used.

Although the present invention and its advantages have been described in detail, it should be understood that various changes, substitutions and alterations can be made herein without departing from the spirit and scope of the invention as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A process for increasing the amount of syngas production in a SMR (Steam Methane Reforming) process by converting carbon dioxide ($CO_2$) to carbon monoxide, the process comprising:

providing an SMR reaction chamber having inputs and an output;

maintaining said SMR reaction chamber at a temperature of between 700° C. and 1000° C.;

providing methane ($CH_4$) to said reaction chamber as a feed-stock;

providing $H_2O$ to said reaction chamber as a feed-stock;

providing a gaseous stream comprising carbon dioxide ($CO_2$) from a source external to an input of said reaction chamber as a feed-stock;

reacting materials in said reaction chamber, the reacting materials consisting essentially of said methane ($CH_4$), said $H_2O$ and said carbon dioxide ($CO_2$) to form syngas comprising carbon monoxide (CO) and hydrogen ($H_2$), said syngas being formed by combing said methane ($CH_4$) with said $H_2O$, and by combining said methane ($CH_4$) with said carbon dioxide ($CO_2$), and wherein the amount of any carbon dioxide ($CO_2$) that does not combine with said methane ($CH_4$) being less than the amount of carbon dioxide $CO_2$ provided in said gaseous stream to said reactor; and discharging said formed syngas at said output.

2. The process of claim 1, wherein said $H_2O$ provided as a reactant into said reaction chamber is steam.

3. The process of claim 1, wherein said reaction chamber is maintained at a temperature of about 870° C.

4. The process of claim 1, wherein said discharged carbon monoxide and hydrogen of said syngas are provided to a bio-catalytic reactor to produce Ethanol or Methanol.

5. The process of claim 4, wherein said bio-catalytic reactor is a Fischer-Tropsch synthesis reactor.

6. The process of claim 4, wherein an output of said bio-catalytic reactor is provided to another bio-catalytic reactor to provide additional Ethanol or Methanol.

7. A process for increasing the amount of syngas production in an SMR process and for consuming carbon dioxide ($CO_2$), the process comprising:

providing an SMR reaction chamber having inputs and an output;

maintaining said SMR reaction chamber at a temperature of between 700° C. and 1000° C.;

providing methane ($CH_4$) to an input of said reaction chamber as a feed-stock;

providing $H_2O$ to an input of said reaction chamber as a feed-stock;

introducing a gaseous stream containing carbon dioxide ($CO_2$) from a source external to an input of said reaction chamber as a feed-stock;

reacting materials in said SMR reaction chamber, wherein the reacting materials consisting essentially of said methane ($CH_4$), said $H_2O$ and said carbon dioxide ($CO_2$) $CO_2$ to form a syngas output comprising carbon monoxide (CO), hydrogen ($H_2$) and unreacted carbon dioxide ($CO_2$), said syngas being formed by combing said methane ($CH_4$) with said $H_2O$ and by combining said methane ($CH_4$) with said ($CO_2$), such that the amount of unreacted carbon dioxide ($CO_2$) in said syngas is less than the amount of carbon dioxide introduced in said reaction chamber by said gaseous stream;

discharging said formed syngas at an output.

8. The process of claim 7, wherein said formed syngas comprising carbon monoxide and hydrogen is provided to a bio-catalytic reactor to produce Ethanol or Methanol.

9. The process of claim 7, wherein an output of said bio-catalytic reactor is provided to another bio-catalytic reactor to produce additional Ethanol or Methanol.

10. The process of claim 7, wherein said $H_2O$ provided as a reactant into said reaction chamber is steam.

11. The process of claim 7, wherein said reaction chamber is maintained at a temperature of about 870° C.

12. The process of claim 8, wherein said bio-catalytic reactor is a Fischer-Tropsch synthesis reactor.

13. The process of claim 4, wherein said bio-catalytic reactor produces a tail gas containing carbon dioxide ($CO_2$) and further comprising recycling said carbon dioxide ($CO_2$) to said SMR reaction chamber.

14. The process of claim 5, wherein said Fischer-Tropsch synthesis reactor produces a tail gas containing carbon dioxide ($CO_2$) and further comprising recycling said carbon dioxide ($CO_2$) to said SMR reaction chamber.

15. The process of claim 7 wherein said unreacted carbon dioxide ($CO_2$) is recycled to said SMR reaction chamber.

16. The process of claim 1 wherein said carbon dioxide ($CO_2$) that does not combine with said methane ($CH_4$) is recycled to said SMR reaction chamber.

17. The process of claim 8, wherein said bio-catalytic reactor produces a tail gas containing carbon dioxide ($CO_2$) and further comprising recycling said carbon dioxide ($CO_2$) to said SMR reaction chamber.

18. The process of claim 12, wherein said Fischer-Tropsch synthesis reactor produces a tail gas containing carbon dioxide ($CO_2$) and further comprising recycling said carbon dioxide ($CO_2$) to said SMR reaction chamber.

* * * * *